(12) United States Patent
Hossainy et al.

(10) Patent No.: US 10,099,431 B2
(45) Date of Patent: Oct. 16, 2018

(54) METHOD TO INCREASE RADIAL STRENGTH OF A BIORESORBABLE SCAFFOLD

(71) Applicant: Abbott Cardiovascular Systems Inc., Santa Clara, CA (US)

(72) Inventors: Syed F. A. Hossainy, Hayward, CA (US); Manish B. Gada, Santa Clara, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 318 days.

(21) Appl. No.: 14/832,283

(22) Filed: Aug. 21, 2015

(65) Prior Publication Data

US 2017/0049593 A1 Feb. 23, 2017

(51) Int. Cl.
| | |
|---|---|
| *B29C 49/04* | (2006.01) |
| *B29C 69/00* | (2006.01) |
| *B29C 55/26* | (2006.01) |
| *A61F 2/915* | (2013.01) |
| *B29K 67/00* | (2006.01) |
| *B29L 31/00* | (2006.01) |

(52) U.S. Cl.
CPC ............ *B29C 69/001* (2013.01); *A61F 2/915* (2013.01); *B29C 55/26* (2013.01); *A61F 2002/91533* (2013.01); *A61F 2002/91558* (2013.01); *A61F 2210/0004* (2013.01); *A61F 2210/0071* (2013.01); *A61F 2240/001* (2013.01); *B29K 2067/046* (2013.01); *B29K 2995/004* (2013.01); *B29K 2995/0056* (2013.01); *B29K 2995/0077* (2013.01); *B29K 2995/0088* (2013.01); *B29K 2995/0097* (2013.01); *B29L 2031/7534* (2013.01)

(58) Field of Classification Search
CPC ................................ B29C 55/26; B29C 55/22
See application file for complete search history.

(56) References Cited

U.S. PATENT DOCUMENTS

| | | | |
|---|---|---|---|
| 7,297,758 B2 | 11/2007 | Gale et al. | |
| 2007/0025399 A1 | 2/2007 | Keating | |
| 2007/0032634 A1 | 2/2007 | Gale et al. | |
| 2008/0169582 A1 | 7/2008 | Vipul Bhupendra et al. | |
| 2009/0012598 A1* | 1/2009 | Abbate | A61F 2/915 623/1.15 |
| 2009/0148492 A1* | 6/2009 | Dave | A61B 17/0057 424/423 |

(Continued)

FOREIGN PATENT DOCUMENTS

| | | |
|---|---|---|
| EP | 1 872 808 | 1/2008 |
| WO | WO 2007/142736 | 12/2007 |

(Continued)

*Primary Examiner* — Galen H Hauth
(74) *Attorney, Agent, or Firm* — Squire Patton Boggs (US) LLP

(57) ABSTRACT

Methods of fabricating a polymer scaffold with increased radial strength including steps of elongation or strain of a biaxially oriented tube and annealing or thermal processing of the strained tube at a constant strain are disclosed. The steps of elongation and thermal processing increase axial direction chain orientation and lamellar crystal growth, increase radial strength, and decrease the thickness of the tube. The method allows fabrication of a scaffold with thinner struts which provide sufficient radial strength.

16 Claims, 7 Drawing Sheets

(56) References Cited

U.S. PATENT DOCUMENTS

| | | | |
|---|---|---|---|
| 2010/0036478 A1* | 2/2010 | Wang | A61L 31/06 623/1.15 |
| 2011/0001271 A1 | 1/2011 | Hossainy et al. | |
| 2011/0260352 A1 | 10/2011 | Fuh-Wei et al. | |
| 2012/0271396 A1 | 10/2012 | Zheng et al. | |
| 2013/0331927 A1* | 12/2013 | Zheng | A61F 2/82 623/1.19 |
| 2015/0230946 A1* | 8/2015 | Al-Lamee | A61F 2/82 623/1.15 |
| 2015/0367554 A1* | 12/2015 | Klausen | B29C 49/04 604/264 |
| 2016/0045344 A1 | 2/2016 | Yan et al. | |
| 2016/0081817 A1 | 3/2016 | Errico et al. | |

FOREIGN PATENT DOCUMENTS

| | | |
|---|---|---|
| WO | WO 2010/017090 | 2/2010 |
| WO | WO 2010/019448 | 2/2010 |

\* cited by examiner

METHOD TO INCREASE RADIAL STRENGTH OF A BIORESORBABLE SCAFFOLD

BACKGROUND OF THE INVENTION

Field of the Invention

This invention relates to fabricating polymeric medical devices, in particular, bioresorbable stents or stent scaffolds.

Description of the State of the Art

This invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. A medicated stent may be fabricated by coating the surface of either a metallic or polymeric scaffold with a polymeric carrier that includes an active or bioactive agent or drug. Polymeric scaffolds may also serve as a carrier of an active agent or drug. An active agent or drug may also be included on a scaffold without being incorporated into a polymeric carrier.

Stents are generally made to withstand the structural loads, namely radial compressive forces, imposed on the scaffold as it supports the walls of a vessel. Therefore, a stent must possess adequate radial strength if its function is to support a vessel at an increased diameter. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading or pressure, which if exceeded, creates a yield stress condition resulting in the stent diameter not returning to its unloaded diameter, i.e., there is irrecoverable deformation of the stent. See, T. W. Duerig et al., Min Invas Ther & Allied Technol 2000: 9(3/4) 235-246. Stiffness is a measure of the elastic response of a device to an applied load and thus will reflect the effectiveness of the stent in resisting diameter loss due to vessel recoil and other mechanical events. Radial stiffness can be defined for a tubular device such as stent as the hoop force per unit length (of the device) required to elastically change its diameter. The inverse or reciprocal of radial stiffness may be referred to as the compliance. See, T. W. Duerig et al., Min Invas Ther & Allied Technol 2000: 9(3/4) 235-246.

When the radial yield strength is exceeded, the stent is expected to yield more severely and only a minimal force is required to cause major deformation. Radial strength is measured either by applying a compressive load to a stent between flat plates or by applying an inwardly-directed radial load to the stent.

Some treatments with stents require its presence for only a limited period of time. Once treatment is complete, which may include structural tissue support and/or drug delivery, it may be desirable for the stent to be removed or disappear from the treatment location. One way of having a stent disappear may be by fabricating a stent in whole or in part from materials that erode or disintegrate through exposure to conditions within the body. Stents fabricated from biodegradable, bioabsorbable, bioresorbable, and/or bioerodable materials such as bioabsorbable polymers can be designed to completely erode only after the clinical need for them has ended.

In addition to high radial strength, a vascular scaffold must have sufficient resistance to fracture or sufficient toughness. A vascular scaffold is subjected to a large deformation during use, in particular, when it is crimped to a delivery diameter and when it is deployed. A scaffold may be susceptible to fracture when in use which can negatively impact performance and even lead to device failure.

It is advantageous for vascular scaffolds to have thin struts while maintaining adequate radial strength. Thin struts lead to a lower profile device in the crimped state for better deliverability. After implantation, neointima proliferates until stent struts are covered. Consequently, thinner struts have less neointimal formation and less area obstruction of the vessel. Lastly, thin struts disturb blood flow less and are less thrombogenic. However, polymer based materials can be orders of magnitude lower in strength in terms of ultimate strength and stiffness compared to metallic alloys. Fabricating a polymer-based scaffold that has sufficiently high radial strength at strut thicknesses comparable to current metallic stents is therefore a challenge.

SUMMARY OF THE INVENTION

Embodiments of the present invention include a method of a fabricating a scaffold comprising: providing a tube having an initial diameter made of a bioresorbable polymer; radially expanding the tube from the initial diameter to an expanded diameter, wherein the expanded tube has a thickness; elongating the expanded tube to a predetermined axial strain along its cylindrical axis by applying a tensile force to the expanded tube along its cylindrical axis, wherein the elongating decreases a thickness of the tube; thermally processing the elongated tube while the tube is fixed at the predetermined axial strain for a selected time at a temperature between a glass transition temperature (Tg) of the polymer and a melting temperature (Tm) of the polymer, wherein a thickness of the thermally processed tube is less than the thickness of the expanded tube; and cutting a scaffold pattern in the thermally processed tube to form a scaffold.

Embodiments of the present invention include a method of a fabricating a scaffold comprising: providing a biaxially oriented tube; elongating the biaxially oriented tube to a predetermined axial strain along its cylindrical axis which decreases a diameter and thickness of the tube; thermally processing the elongated tube while the tube is fixed at the predetermined strain for a selected time at a temperature between a glass transition temperature (Tg) of the polymer and a melting temperature (Tm) of the polymer, wherein a thickness of the thermally processed tube is less than the thickness of the expanded tube; restricting the decrease in diameter during elongation and thermal processing to a selected diameter by a radially outward force; and cutting a scaffold pattern in the thermally processed tube to form a scaffold.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION OF THE INVENTION

In many treatment applications using stents, stents expand and hold open narrowed portions of blood vessels. As indicated, to achieve this, the stent must possess a radial strength in an expanded state that is sufficiently high and sustainable to maintain the expanded vessel size for a period of weeks or months. This generally requires a high strength and rigid material. In the case of bioresorbable polymer stents or scaffolds, bioresorbable polymers that are stiff and rigid have been proposed and used in stents for coronary intervention. Such polymers are stiff or rigid under physiological conditions within a human body. These polymers tend to be semicrystalline polymers that have a glass transition temperature (Tg) in a dry state sufficiently above human body temperature (approximately 37° C.) that the polymer is stiff or rigid at these conditions. Polylactide and polylactide based polymers such as poly(L-lactide) are examples of such semicrystalline polymers that have been proposed and used as a stent or scaffold materials.

Figure 1:
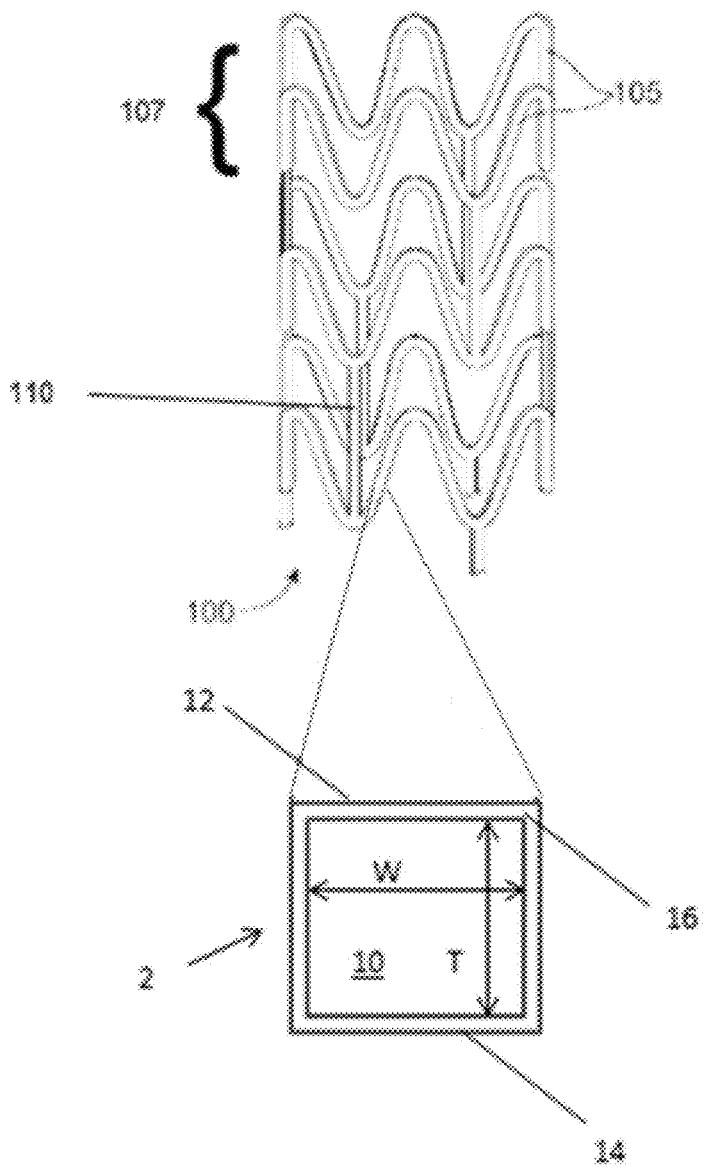
FIG. 1A depicts a view of an exemplary scaffold.
FIG. 1B show a cross-selection of a strut of the scaffold of FIG. 1A.

FIG. 1A depicts a view of an exemplary scaffold 100 which includes a pattern or network of interconnecting structural elements 105. FIG. 1A illustrates features that are typical to many stent patterns including cylindrical rings 107 connected by linking elements 110. The cylindrical rings are load bearing in that they provide radially directed force in response to an inward force on the scaffold. The linking elements generally function to hold the cylindrical rings together. Exemplary scaffolds are disclosed in US 2008/0275537, US 2011/0190872, and US 2011/0190871. Any of the patterns disclosed in these references are applicable to the inventive scaffolds.

FIG. 1B show a cross-selection of a strut 2 showing the polymer scaffold body, polymer backbone, or core of the strut surrounded by a drug/polymer coating or matrix 16. The cross-section of the strut has an abluminal or outer surface or side 12 that faces the vessel wall and a luminal or inner surface or side 14 that faces the lumen of the vessel. The strut cross-section shown is shown to be rectangular with a width (W) and thickness (T). The slight curvature at the inner and outer surfaces due to the tubular geometry is not shown. The present invention is not limited to this scaffold pattern or type of pattern and is applicable to any pattern.

Fabricating a vascular scaffold from such materials with sufficient fracture toughness or fracture resistance is challenging due to their brittle nature. Vascular scaffolds are subjected to deformation and stress during manufacture when crimped to a delivery diameter, when deployed or expanded from a delivery diameter to a deployment diameter, and during use after deployment. As a result, vascular scaffolds are susceptible to fracture during manufacture (particularly during crimping), deployment, and use. The fracture toughness is important in reducing material-level damage during crimping and in vitro/in vivo deployment of a bioresorbable scaffold. The reduced damage allows achievement of a sufficiently high radial strength with a reduced strut thickness and cross-section.

It is a continuing challenge to develop new materials and processing methods for vascular scaffolds with sufficiently high radial strength, particularly during crimping and deployment or expansion.

Another challenge in making a bioabsorbable polymer scaffold relates to the lower strength to weight ratio of polymers compared to metals. The strength of a scaffold material is proportional to the radial strength of the scaffold. Therefore, polymeric scaffolds require thicker struts than a metallic stent to achieve the radial strength required to provide patency to a blood vessel. Exemplary coronary polymer scaffolds have wall thicknesses from about 150 to 170 microns while coronary metallic stents have strut thicknesses of 60 to 100 microns. It is desirable to have a scaffold profile as low as possible. Thus, making a scaffold with a smaller form factor, i.e., with thinner struts, that provides sufficient radial strength is a challenge. The thickness of a strut may refer to a thickness at a particular location or an average thickness over any length or over the entire scaffold. Strut thickness of scaffolds and tubing from which scaffolds are fabricated may be measured using OptiGauge™ from Lumetrics of Rochester, N.Y. Strut thickness is also referred to as wall thickness.

The fabrication of a bioresorbable scaffold may include the following processes or steps: forming a hollow, thin-walled polymeric tube (i.e., pre-cut tube), preferably with no holes in the walls; processing that increases the strength of the polymer of the scaffold body and also the radial strength of the scaffold; forming a stent scaffolding made up of thin struts from the tube by laser machining a stent pattern in the tube; optionally forming a therapeutic coating over the scaffolding; crimping the scaffold over a delivery balloon, and sterilization of the scaffold using radiation, an ethylene oxide process, or some other sterilization process. Detailed discussion of the manufacturing processes of a bioabsorbable stent can be found elsewhere, e.g., U.S. Patent Publication Nos. 2007/0283552 and 2012/0073733.

A pre-cut tube can be formed by a melt processing method such as extrusion or injection molding. In extrusion, for example, a polymer resin is fed into an extruder inlet and conveyed through the extruder barrel as a melt above the melting temperature (Tm) of the polymer. For example, the temperature of the melt in the extruder may be 180 to 250° C. At the end of the extruder barrel, the polymer melt is forced through a die to form a tubular film which is longitudinally drawn and cooled to form the tube. The degree of crystallinity of the tube formed from the melt processing may be 0%, less than 5%, less than 10%, 5 to 10%, or 10 to 15%.

Figure 2:
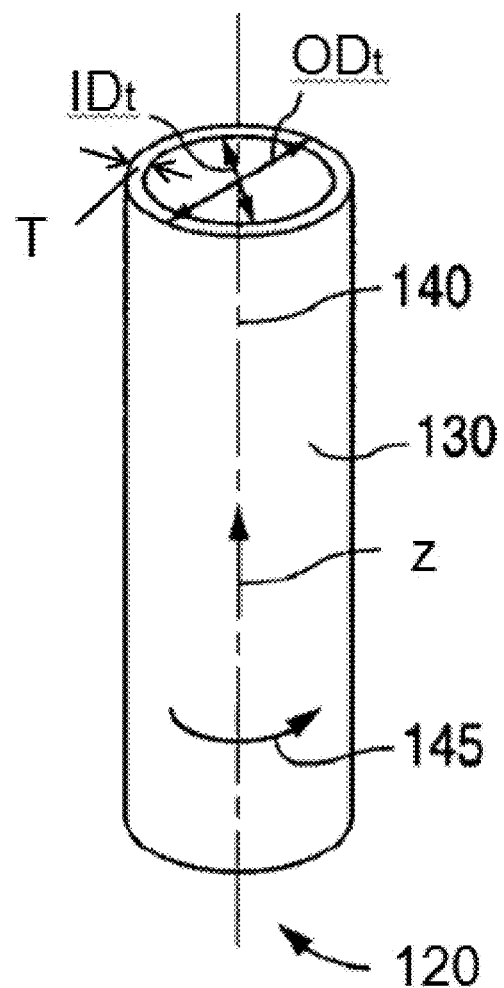
FIG. 2 depicts a polymer tube.

FIG. 2 depicts a polymer tube. Tube 120 is a cylinder with an outside diameter ODt and an inside diameter IDt. Tube 120 has a surface 130 and a cylindrical or longitudinal axis z. A thickness (T) of tube 120 is ODt–IDt. When referred to below, unless specified, the "diameter" of the tube may refer to either the outside or inside diameter of tube.

A polymer resin is the raw material used for the melt processing for forming the polymeric tube. In order to provide the high molecular weight of the finished sterilized product, the resin has a much higher molecular weight than the finished product. The molecular weight of the resin may be expressed in terms of the intrinsic viscosity (IV) in dL/g. The IV of a polymer resin may be higher than 5 dL/g, greater than 7 dL/g greater than 8 dl/g, 4 to 8 dL/g, 5 to 8 dL/g, 4 to 6 dL/g, 6 to 8 dL/g, or 5 to 7 dL/g.

A processing step that increases the strength of the polymer may include a step of inducing biaxial orientation of polymer chains in the polymer tube to create a biaxially oriented polymer tube. A biaxially oriented polymer includes strong preferential orientation of the polymer chains in the hoop or circumferential direction of the tube as shown by arrow 145 in FIG. 2 and preferential orientation along the axial direction as shown by "z" in FIG. 2. A biaxially oriented tube may be made by radially expanding a tube from an initial diameter to a larger diameter. The larger diameter tube may then be cut to form a scaffold.

The radial expansion increases the radial strength both through an increase in crystallinity by strain induced crystallization and induced polymer chain and crystal alignment in the circumferential or hoop direction. The radial expansion process may be performed by several processes including blow molding (e.g., US 2011/0066222) or by expanding over a mandrel (e.g., WO 2014/045068). In blow molding, the pre-cut tube is disposed within a mold and heated to a temperature between Tg and Tm and expanded by increasing a pressure inside of the tube.

Embodiments of the present invention are directed to methods of fabricating bioresorbable vascular scaffolds with processing steps that increase the radial strength of the scaffold. The methods may be used to fabricate scaffolds having thin struts and have sufficient radial strength to support a vessel upon deployment.

Aspects of the invention include steps of elongation or strain of a biaxially oriented tube and annealing or thermal processing of the strained tube at a constant strain. The additional steps of elongation and thermal processing steps increase axial direction chain orientation and lamellar crystal growth. The additional steps also decrease the thickness of the struts so the method provides a scaffold with thin struts that provides adequate radial strength.

The additional steps may provide such benefits with bioresorbable polymer s of any polymer molecular weight, for example, a resin or tube in the range of weight average molecular weight (Mw) of 200K to 600 kDa. The additional steps may also work synergistically with higher molecular weight polymers, for example, 600 to 1500 kDa to increase radial strength. The synergy may result for at least two reasons. First, the elongation/thermal processing results in greater chain entanglement and greater biaxial orientation that both result in greater radial strength which allows for reduced strut thickness with adequate radial strength. Second, longer polymer chains reduce high energy boundaries between organized domains, e.g., crystalline or oriented amorphous domains. This results in ductile failure behavior which provides a higher expandability or larger expansion diameter limit upon deployment.

The expansion capability or expandability of a scaffold refers generally to the ability to a scaffold to be expanded from a crimped state (e.g., in saline or bodily fluid) to a deployed state without failure and/or with the capability to provide a clinical useful radial strength. The degree may be quantified by the maximum diameter that the scaffold may be deformed or expanded without failure or the diameter at which the scaffold fails. The expansion capability may be inferred from a post-dilation-to-fracture test. For example, the maximum expansion diameter of a stent or scaffold deployed from a crimped stent or scaffold profile (e.g., less than 0.049, or 0.05 in) may be 3.75 to 4 mm, 4 to 4.5 mm, 4.5 to 5 mm, 5 to 5.5 mm, or greater than 5.5 mm.

Embodiments of the invention include a method of fabricating a scaffold which includes providing an initial tube having an initial diameter made of a bioresorbable polymer. The initial tube is radially expanded from the initial diameter to an expanded diameter. The expanded tube has an expanded thickness, which is less than the thickness of the provided tube. As described above, the radial expansion may be performed in a temperature range of Tg to Tm of the bioresorbable polymer.

For a polymer that is phase-separated and shows two distinct Tgs, the Tg is to be considered the higher of the Tgs.

After cooling or allowing the tube to cool to below Tg or to ambient temperature, the expanded tube is elongated to a predetermined axial strain along its cylindrical or longitudinal axis by applying a tensile force to the expanded tube along its axis. The elongation is performed without any radial expansion or increase in diameter of the tube. The elongation increases a length of the tube and decreases a thickness of the tube to an elongated thickness. In some aspects, the tube is heated to a temperature between Tg and Tm prior to elongation. This temperature may be in the same range as given below for the thermal processing. The tube is heated from an ambient temperature or a temperature below the Tg to the elongation temperature.

The elongated tube is then thermally processed or annealed while it is maintained at the predetermined axial strain for a selected time at a temperature between a Tg and Tm of the polymer. The thermal processing is performed immediately upon elongating without reducing the tube temperature below the Tg of the polymer. The thermal processing may be performed without any radial expansion or increase in diameter of the tube. The final thickness of the tube after thermal processing is less than the expanded thickness.

A scaffold is fabricated from the thermally processed tube, for example, but cutting a scaffold pattern in the tube. The scaffold may have a strut thickness at or close to the final thickness, e.g., within ±5% of the final thickness. The scaffold may optionally be coated with a drug delivery coating and then crimped over a delivery balloon.

The provided tube may be formed by solvent processing (e.g., spraying or dipping) or melt processing, (e.g., extrusion or injection molding). The provided tube may have an ID of 0.25 to 1 mm, or more narrowly, 0.35 to 0.5 mm and a wall thickness of 0.3 to 1.5 mm, or more narrowly, 0.5 to 1 mm. The crystallinity of the provided tube may be 15% or lower, such as less than 10% or less than 5%.

Figure 3A:
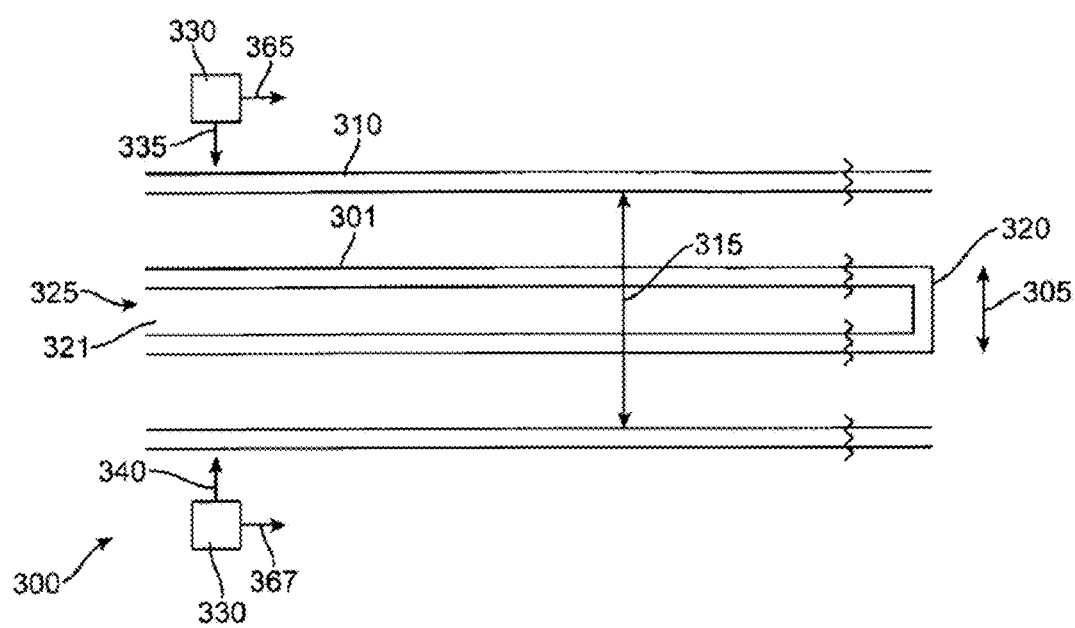
FIGS. 3A-C depict a schematic blow molding system which illustrates radially expanding a polymer tube with blow molding.
Figure 3B:
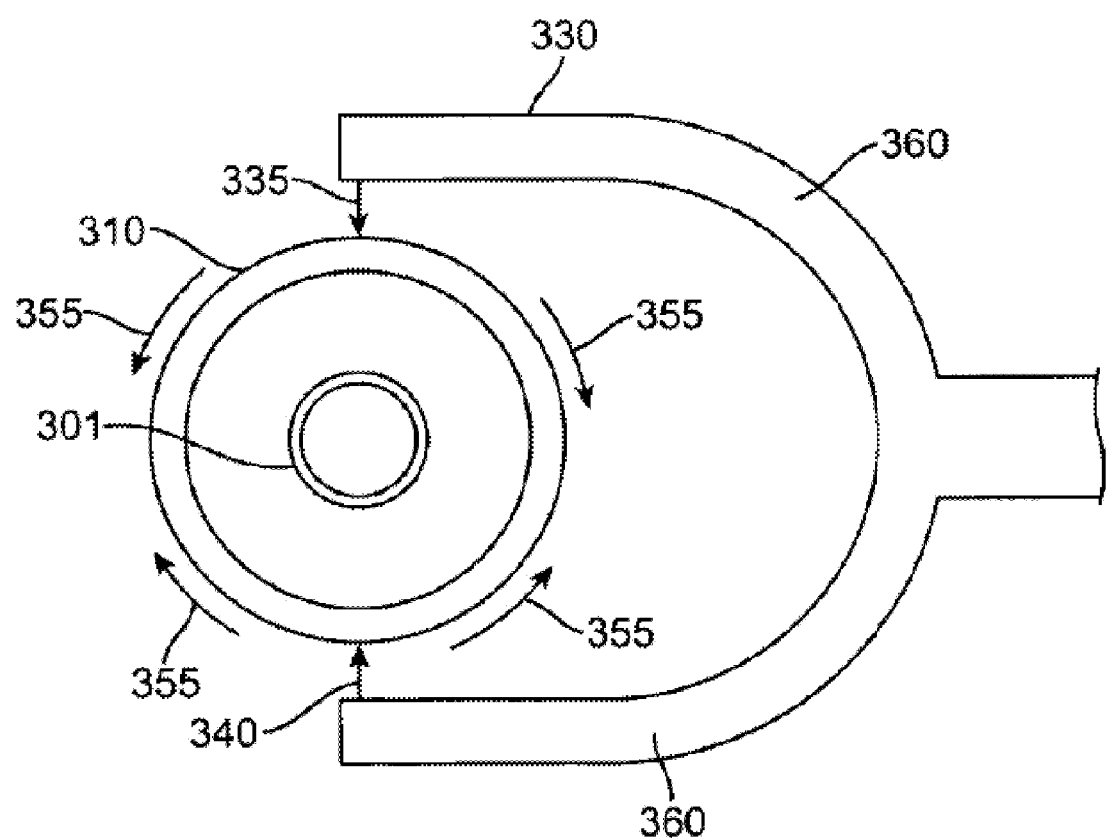
Figure 3C:
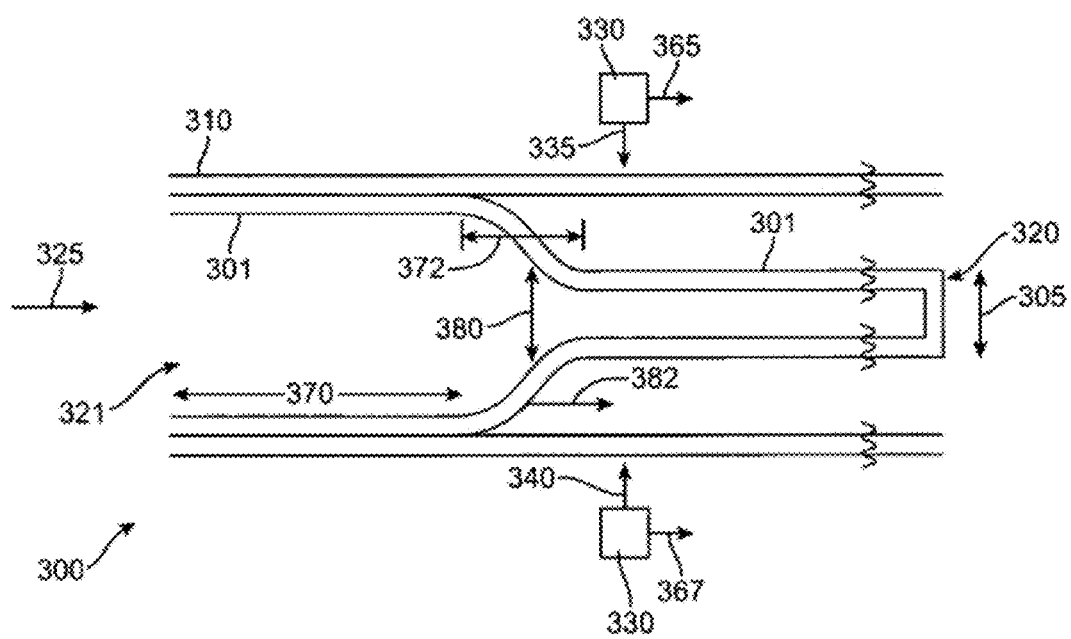

The extruded tube may be radially expanded by blow molding. FIGS. 3A-C depict a schematic blow molding system 300 which illustrates radially expanding a polymer tube with blow molding. FIG. 3A depicts an axial cross-section of a polymer tube 301 with an outside diameter 305 positioned within a mold 310. Mold 310 limits the radial expansion of polymer tube 301 to a diameter 315, the inside diameter of mold 310. Polymer tube 301 may be closed at a distal end 320. A gas may be conveyed, as indicated by an arrow 325, into an open proximal end 321 of polymer tube 301 to increase an internal pressure within tube 301 to radially expand tube 301. A tensile force can be applied at proximal end 321, a distal end 320, or both.

Polymer tube 300 is heated by a nozzle 330 with fluid ports that direct a heated fluid at two circumferential locations of mold 310, as shown by arrows 335 and 340. FIG. 3B depicts a radial cross-section showing tube 301, mold 310, and nozzle 330 having structural members 360. Additional fluid ports can be positioned at other circumferential locations of mold 310. The heated fluid flows around tube 310, as shown by arrows 355, to heat mold 310 and tube 301 to a temperature above a Tg of the polymer of tube 301.

Nozzle 355 translates along the longitudinal axis of tube 301 and mold 310 as shown by arrows 365 and 367. As nozzle 330 translates along the axis of mold 310, tube 301 radially expands. The increase in temperature of tube 301 and the increased pressure cause expansion of tube 301, as depicted in FIG. 3C.

FIG. 3C depicts system 300 with an expanding section 372 and an expanded section 370 of tube 301. Section 372 expands radially as shown by an arrow 380. Expanded section 370 has an outside diameter the same as the outside diameter of mold 310.*

The tube may also be subjected to a tensile force in the axial direction which may axial strain the tube during the radial expansion. The percent axial strain, as defined below, may be less than 50%, or more narrowly, 10 to 50%, or 20 to 30%.

The radial strain of an expanded tube may be define as: % $RS=(D_{expanded}\ ID_{initial}-1)\times 100\%$. The % RS may be 300±10%, 400±10%, 500±10%, 300 to 400%, 400 to 500%, 500 to 550%, 550 to 600%, or greater than 600%.

A radially expanded tube may have an ID of 2.5 to 5 mm, or more narrowly, 2.5 to 4 mm, or 3 to 4 mm. In some aspects, the thickness of the expanded tube may be greater than 140 microns, for example 140 to 200 microns, or more narrowly, 140 to 170 microns. In other aspects, the thickness of the expanded tube may be greater than 200 microns, for example, 200 to 300 microns.

Exemplary ranges for the temperature of the radial expansion may be Tg to Tg+10° C., Tg to Tg+20° C., or Tg+5° C. to Tg+20° C. For example, for a tube made of PLLA or a blend of PLLA having a high percentage of PLLA (e.g., greater than 80 wt %), the temperature of radial expansion may be 60 to 90° C., or more narrowly 60 to 70° C., 70 to 80° C., or 80 to 85° C. After the tube or section of tube is radially expanded, the expanded tube or section is immediately cooled or allowed to cool to below Tg and to ambient temperature.

The radial expansion process may increase the crystallinity of the tube through strain induced crystallization to 25% or greater, such as, 25 to 55%, 25 to 40%, 40 to 50%, or greater than 50%.

The elongation step is performed after the radially expanded tube is cooled to below Tg or ambient temperature. The elongation may be performed by applying an axially directed tensile force on one end with the other end of the tube fixed. Alternatively, the axially directed tensile force may be applied at both ends.

Figure 4A:
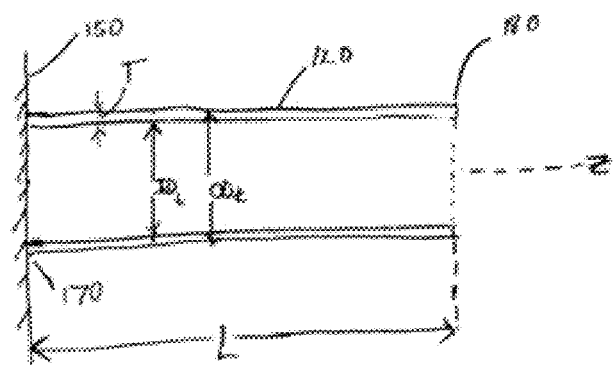
FIGS. 4A-B depict a schematic illustration of the elongation and thermal processing of a tube.
Figure 4B:
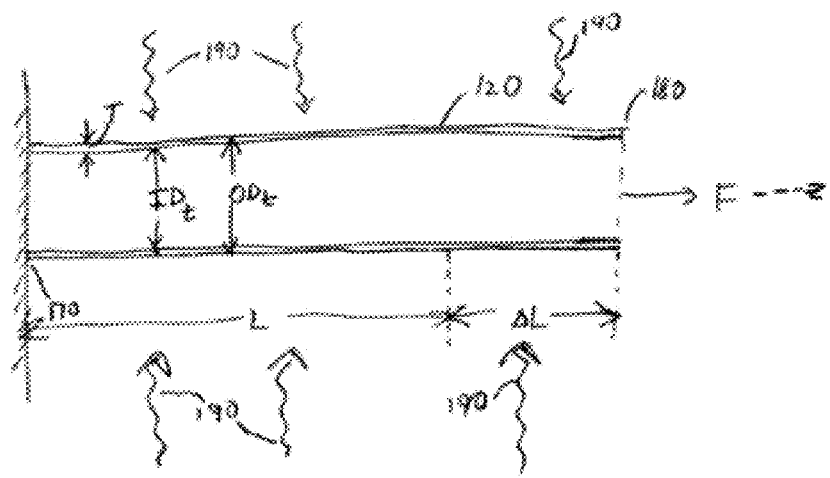

FIGS. 4A-B depicts a schematic illustration of the elongation and thermal processing of a tube 120. FIG. 4A shows a tube 120 in an initial state with a length L prior to elongation with end 170 of tube 120 fixed at a boundary 150. End 170 may be fixed for example by a clamp. End 180 of tube 120 is configured to move axially away from boundary 150 when tube 120 is deformed by an axially directed force away from boundary 150. FIG. 4B depicts tube 120 elongated to a length L+ΔL by an applied force F along the axial direction z. Tube 120 is heated by warm air 190. The elongation may be performed using a tensile testing system from, for example, Instrom, Norwood, Mass.

The axial strain is defined as the percent change in length ΔL per unit of the initial length L of the tube:

$$\text{axial strain} = 100\% \times \Delta L/L\text{initial}$$

$$= 100\% \times [(L\text{elongated} - L\text{initial})/L\text{initial}].$$

The initial length of the tube is the length of the expanded tubing. The axial strain of the process may be 1 to 50%, or more narrowly, 1 to 5%, 5 to 10%, 10 to 20%, 20 to 30%, or 30 to 50%.

The elongation and thermal processing may increase the crystallinity of the tube by 1 to 10%, or more narrowly, by 5 to 10% of the crystallinity of the tube at the end of the radial expanding step.

As the tube is strained, the thickness of the tube is expected to decrease in the absence of any radially outward force on the tube. The axial strain of the process may be determined by a desired thickness of the tube. That is, an axial strain is selected that results in the desired thickness of the tube. The desired thickness after elongation to the axial strain may be 80 to 120 microns, or more narrowly 90 to 100 microns, 95 to 105 microns, 90 to 110 microns, or 100 to 110 microns.

The temperature of the thermal processing or annealing may be Tg to Tg+10° C., Tg to Tg+20° C., or Tg+5° C. to Tg+15° C. For example, for a tube made of PLLA or a blend of PLLA having a high percentage of PLLA (e.g., greater than 80 wt %), the temperature of radial expansion may be 60 to 90° C., or more narrowly 60 to 70° C., 70 to 80° C., or 80 to 85° C.

The time of thermal processing may be 1 to 30 min, 1 to 10 min, 5 to 10 min, 10 to 20 min, or 20 min to 30 min. The time and temperature of the thermal processing may be selected to obtain a desired value of a mechanical property of the polymer of the tube or scaffold, a desired value of a scaffold property of the scaffold, a desired value of the crystallinity of the tube, a desired value of a geometrical property of the scaffold, or any combination thereof.

The mechanical property may be the strength. The thermal processing may increase the strength of the polymer by 1 to 5%, 5 to 10%, or 10 to 20%.

The scaffold property may be the radial strength of a scaffold formed from the elongated/thermally processing tube. A desired value of radial strength may be a value sufficient to maintain a lumen at deployment diameter in a blood vessel. A desired value of radial strength may be at least 650 mm Hg, at least 800 mm Hg, at least 1000 mm Hg, 400 to 600 mm Hg, 500 to 1200 mm Hg, 700 to 900 mm Hg, or 800 to 1300 mm Hg.

The geometrical parameter may be the thickness of the tube which may increase, decrease, or remain the same during the thermal processing. The desired thickness as a result of the thermal processing may be in any of the ranges disclosed at the end of the elongation.

The thermal processing of the tube may be performed by heating the tube with warm air while the tube is maintained at a fixed axial strain. A nozzle or nozzles may blow warm air at a selected temperature at the outer surface of the strained tube. Alternatively or additionally, the nozzle may blow warm air into the tube at the inner surface of the tube. The strained tube may also be heated by a lamp that directs visible, infrared, or UV radiation at the tube. A conductive heating element or elements disposed near the outside surface of the tube or within the tube may also be used for heating the tube. In other aspects, the tensile strained tube is subjected to a heat flux from a moving heat source axially for a fixed amount of time. For example, a nozzle blowing hot air at the tube may be translated axially back and forth from one end of the tube to the other. Alternatively, a conductive heating element can likewise be translated to heat the tube.

In some aspects, when the thermal processing is completed, the tube is maintained at the axial strain until the temperature of the tube is cooled to below the Tg and to ambient temperature. In other aspects, when the thermal processing is completed, the tube is no longer maintained, fixed, or restrained at the axial strain and cools from the thermal processing temperature to below Tg and to ambient temperature.

A tradeoff is expected between the benefits to radial strength from the elongation/thermal processing and potential loss of circumferential orientation of polymer chains during this processing which may have a negative effect on radial strength. The tradeoff is controlled by the time and temperature of the thermal processing. The higher the temperature, the longer the time, or both increases the loss of circumferential orientation of polymer chains and potential loss of radial strength. Thus, the time, temperature, or both of the processing can be selected to provide the desired scaffold properties.

As indicated, without a diameter constraint, the tube diameter decreases as the tube is elongated. In certain aspects, the elongation and thermal processing are performed with no outward radial force that would that would prevent or limit the amount the diameter of the tube decreases as it is elongated and thermally processed.

In some aspects, the amount of decrease in the diameter of the tube may be limited to a selected diameter during the elongation and thermal processing. In other aspects, a change in diameter of the tube is prevented during the elongation and thermal processing. Preventing a decrease in diameter or a decrease in diameter may be limited to a selected diameter by disposing the expanded tube prior to elongation over a tubular mandrel having an outer diameter (ODm) equal to or less than the inner diameter of the expanded tube (IDt). The change in diameter of the tube is limited to ODm. To limit a change in diameter of the expanded tube to less than or equal X %, an ODm of (1−X %)×IDt is used.

A given axial strain can reduce the diameter of the tube to ODm. In some aspects, the axial strain is increased to greater than this given axial strain and the mandrel exerts an outward radial force on the inner surface of the tube which prevents further decrease in the tube diameter and limits the tube diameter to ODm.

The axial strain required for a selected in initial (before elongation) and final (after elongation) state of a tube can be estimated from the initial tube thickness ($T_i$), final tube thickness ($T_f$), initial inside diameter (IDi), and final inside diameter (IDf):

$$\Delta L/L = (T_i/T_f) \times (IDi+T_i)/(IDf+T_f) - 1, \qquad \text{EQ. 1}$$

or since $IDi \gg T_i$ and $IDf \gg T_f$, $$\Delta L/L \sim (T_i/T_f) \times (IDi/IDf) - 1 \qquad \text{EQ. 2}$$

EQ. 1 is derived under the assumption of no volume change upon elongation. EQ. 1 shows that the axial strain for a given change in thickness is a minimum for a constraint of no diameter change upon elongation (IDi=IDf) since IDi>IDf when a diameter change is allowed.

The inventors believe that effects such as stress relaxation may contribute to dimensional changes when the tube is elongated and during thermal processing. For example, as a result of positive or negative contributions to thickness during elongation, the axial strain required for a selected change in thickness will be lower with positive contributions and higher with negative contributions than that estimated by the EQ. 1 or EQ. 2. Likewise, as a result of an increase or decrease in thickness of the tube during thermal processing, the axial strain required for a selected change in thickness will be lower with an increase in thickness and higher with a decrease in thickness than that estimated by the EQ. 1 or EQ. 2.

Figure 5A:
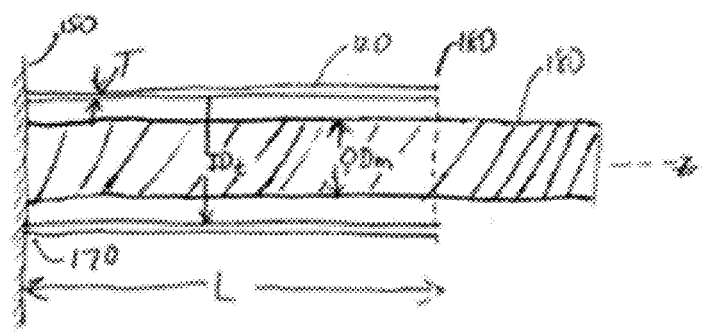
FIGS. 5A-B depict a schematic illustration of the elongation and thermal processing of a tube over a mandrel.
Figure 5B:
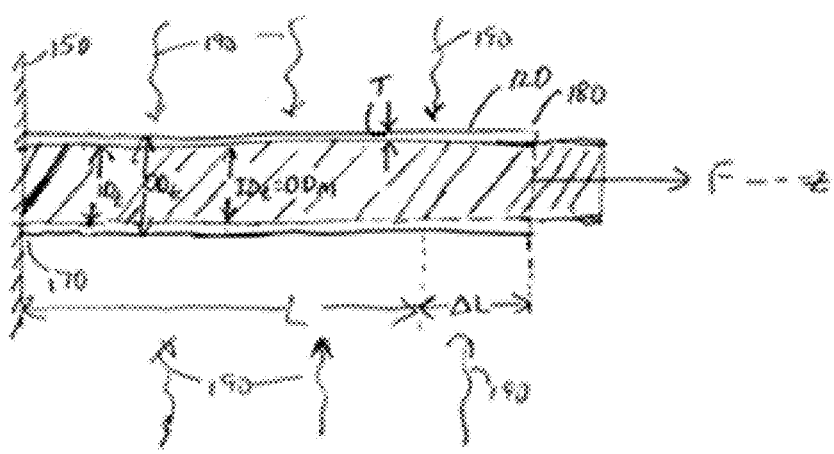

FIGS. 5A-B depict a schematic illustration of the elongation and thermal processing of a tube 120 over a tubular mandrel 180. FIG. 5A shows a tube 120 of length L, an initial state prior to elongation, over mandrel 180, with one end fixed and the other end adapted move axially upon elongation of tube 120. FIG. 5B depicts tube 120 over mandrel 180 elongated to a length L+ΔL by an applied force F in the axial direction z. Tube 120 is heated by warm air 190. The inner diameter of tube 120 (IDt) decreases when elongated. However, the decrease of IDt is limited to the outer diameter of mandrel 180, ODm, with the result that IDt=ODm. Mandrel 180 exerts a radially outward force on tube 120 to prevent a further decrease in the diameter of tube 120.

In some aspects, the IDt may be limited to diameter change of less than 1%. In other aspects, the IDt may be limited to a diameter change of 1 to 30%, or more narrowly, 1 to 5%, 5 to 10%, 10 to 20%, or 20 to 30%. The change in diameter may be less than 2 microns, 2 to 50 microns, 0.01 to 2 microns, 2 to 5 microns, 5 to 10 microns, 10 to 20 microns, 20 to 30 microns, 30 to 40 microns, or 40 to 50 microns.

In some aspects, the mandrel is made of a highly heat conductive material such as a metal, e.g., stainless steel, and the tube is in contact with the metal surface. Alternatively, the mandrel is made of a material that is an insulator such as a plastic or is made of a metal with an insulator, such as a plastic, e.g., a polytetrafluoroethylene such as Teflon. When a highly heat conductive mandrel is used, the mandrel may act as a heat sink and reduce degree of heating of the tube, provide faster cooling of the tube when the heating is removed, or both.

In further embodiments of the invention, the elongation and thermal processing steps can be performed before the radial expanding step. In such embodiments, a provided tube is subjected to the elongation and thermal processing steps as described. After reducing the tube to below the Tg of the polymer or reduced to ambient temperature, the tube is subjected to the radial expansion step.

The scaffold of the invention can include or be made of polymer(s) that are biostable, bioresorbable, bioabsorbable, biodegradable, or bioerodable. Biostable refers to polymers that are not biodegradable. The terms biodegradable, bioresorbable, bioabsorbable, and bioerodable are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, hydrolysis and metabolic processes.

The polymer of the scaffold can include any of the polymers or any combination of the polymers disclosed herein. In particular, the polymer is a lactide or lactic acid polymer which comprises poly(lactic acid) or poly(lactide) ("PLA"). A poly(lactic acid) based polymer (PLA based polymer) can be a polymer which incorporates at least 5% (w/w) of L-lactic acid or D-lactic acid. Polymers include poly(L-lactide) (PLLA), poly(D-lactide), poly(D,L-lactide), poly(D,L-lactide), poly(L-lactide-co-D,L-lactide), poly(L-lactide-co-glycolide), poly(D,L-lactide-co-glycolide), poly(L-lactide-co-caprolactone), poly(D,L-lactide-co-caprolactone), and poly(D, L-lactide) made from polymerization of a racemic mixture of L- and D-lactides. The ratio of D and L lactide in the PLA polymer may be 50:99 molar ratio. The ratio of D, L, and meso lactide in the PLA polymer may be 25:25:50 to 1:1:98 molar ratio.

The polymer of the scaffold may also include homopolymers and copolymers of polyanhydrides, poly(trimethylene carbonate), poly-4-hydroxybutyrate (P4HB), polyhydroxyvalerate (PHV), polyhydroxyhexanoate (PHH), and polyhydroxyoctanoate (PHO).

The polymer of the scaffold may also be a blend of any combination of the polymers described herein. In particular, the polymer may be a blend of polylactide and polycaprolactone (PCL), poly(trimethylene carbonate) (PTMC), polydioxanone (PDS), poly(glycerol sebacate) (PGS), or polybutylene succinate (PBS). The blend ratio of any of the polymers and a polylactide is 1:99 to 30:70 w/w. The polymer of the scaffold may also be a random or block copolymer of polylactide and polycaprolactone, poly(trimethylene carbonate), polydioxanone, poly(glycerol sebacate), or polybutylene succinate. Including such polymers as a blend or copolymer with a PLA polymer may add to ductile failure behavior, hence allowing larger limit of diameter expansion or expandability of a scaffold.

The polymer of the scaffold may also be a blend of polylactide and a copolymer of polylactide and polycaprolactone, poly(trimethylene carbonate), polydioxanone, poly (glycerol sebacate), or polybutylene succinate. For example, the polymer blend may be PLLA+PLLA-co-PCL, PLLA+PLLA-co-PTMC, PLLA+PLLA-co-PDS, PLLA+PLLA-co-PGS, and PLLA+PLLA-co-PBS. The total composition of CL, TMC, DS, GS, or BS in any of these blends may be 1 to 10 wt %, 5 to 10%, or 1 to 5%. The blend of the PLLA and a PLA and the copolymer may include 80 to 99% PLLA, or more narrowly, 85 to 95 wt % PLLA. The copolymer may be 1 to 20 wt %, or more narrowly, 5 to 15% of the blend.

The polymer of the scaffold may have two or phases due to phase separation of immiscible polymers.

Selected ranges of strut thickness of a scaffold include 150 to 170 microns, less than 150 microns, less than 140 microns, less than 130 microns, 80 to 100 microns, 80 to 120 microns, 80 to 90 microns, 90 to 100 microns, 90 to 110 microns, 95 to 100 microns, 100 microns, 110 to 120 microns, or 95 to 105 microns. The thickness may refer to a thickness of a scaffold that is formed by laser cutting a tube just prior to crimping over a balloon or as crimped on the balloon. The thickness may further refer to the thickness of the scaffold formed from laser cutting plus a thickness of a coating over the laser cut scaffold. All or a majority of the struts of the scaffold may have a thickness in the selected range. An aspect ratio of strut width divided by strut thickness may be defined. Selected ranges of this aspect ratio include less than 3, less than 2, less than 1, less than 0.5, greater than 1, 1 to 1.5, 1.5 to 2, 1.5 to 1.8, 1.6 to 1.9, 0.75 to 2, 1.5 to 2.5, 1.7 to 2.3, 1.5 to 2.5, or 2 to 2.5.

The crimped profile of the stent or scaffold may be less than 0.055 in, 0.05 in, less than 0.049 in, 0.05 to 0.055 in, or 0.047 to 0.05 in. The crimped profile refers to an outer diameter of a stent or scaffold crimped over a delivery balloon.

The radial strength of the scaffold can be high enough to provide mechanical support to a vessel after expanding the vessel to an increased diameter or prevent or reduce a decrease in the diameter of the vessel. The scaffold has a crimped state and a deployed state and a radial strength of the scaffold may refer to a radial strength when expanded from the crimped state to the deployed state in saline or bodily fluid at 37° C. The radial strength may be at least the value required to support a vessel at a reference vessel diameter, which is the healthy diameter of a vessel at an implant site. The radial strength is at least 350 mm Hg, at least 500 mm Hg, at least 650 mm Hg, at least 800 mm Hg, at least 1000 mm Hg, 400 to 600 mm Hg, 500 to 1200 mm Hg, 700 to 900 mm Hg, or 800 to 1300 mm Hg.

Drug delivery from the scaffold can be provided from a coating on a surface of the scaffold. The coating may be in the form a neat drug. Alternatively, the coating may include a polymer matrix with the drug mixed or dissolved in the polymer. The polymer matrix can be bioresorbable. Suitable polymers for the drug delivery polymer can include any PLA-based polymers disclosed herein, any other polymers disclosed herein, and copolymers and blends thereof in any combination.

The scaffold can be balloon expandable or self expandable. In the case of a balloon expandable device, the geometry of the device can be an open-cell structure or closed cell structure, each formed through laser cutting a hollow thin-walled tube.

The scaffold is radially expandable at, for example, 37° C. in body fluid or simulated body fluid. When the scaffold is expanded by a balloon, the structural elements plastically deform. The scaffold is expanded to an intended expansion or deployment diameter and retains the intended expansion diameter or a diameter slightly less due to acute recoil inward due to inward pressure from the vessel during the about the first 30 minutes.

In the case of a self-expandable scaffold, when the scaffold is compressed from a fabricated diameter to a delivery diameter on a balloon, the structural elements deform elastically. Therefore, to retain the scaffold at the delivery diameter, the scaffold is restrained in some manner with an inward force, for example with a sheath or a band. The compressed scaffold is expanded to an intended expansion or deployment diameter by removing the inward restraining force which allows the scaffold to self-expand to the intended deployment diameter. The structural elements deform elastically as the device self-expands. If the final expansion diameter is the same as the fabricated diameter, the scaffold does not exert any chronic outward force. If the final expansion diameter is less than the fabricated diameter, the scaffold does exert a chronic outward force.

A stent or scaffold may have lengths of between 8 and 18 mm, 18 and 36 mm, 36 and 40 mm, or between 40 and 200 mm as fabricated or when implanted in an artery. Exemplary lengths include 12 mm, 14 mm, 18 mm, 24 mm, or 48 mm. The scaffold may have a pre-crimping or as-fabricated diameter of 2 to 3 mm, 2.5 to 3.5 mm, 3 to 4 mm, 3 to 5 mm, 5 to 10 mm, 6 to 8 mm, or any value between and including these endpoints. Diameter may refer to the inner diameter or outer diameter of the scaffold. Exemplary diameters include 2.5 mm, 3.0 mm, 3.25 mm, 3.5 mm, 4 mm, 5 mm, or 6 mm.

A crimped scaffold may be packaged and then sterilized with radiation such as electron-beam (E-Beam) radiation or a low temperature ethylene oxide process.

Definitions

"Ambient temperature" is defined as the temperature of a surrounding environment, such as a temperature surrounding a process or experiment that is unaffected by heating or cooling of the process or experiment or a temperature surrounding a patient being treated. The ambient temperature may be defined as 20 to 25° C. or 25 to 30° C.

"Molecular weight" refers to either number average molecular weight (Mn) or weight average molecular weight (Mw). References to molecular weight (MW) herein refer to either Mn or Mw, unless otherwise specified. The Mn may be as measured by Gel Permeation Chromatography with refractive index detection relative to polystyrene standards. Suitable mobile phase solvents are acetone, tetrahydrofuran, chloroform, 1,1,1-trichloroethane, 2,2,2-trifluoroethanol, and hexafluoro-2-propanol, "Semi-crystalline polymer" and other terms relating to crystalline polymers may be as defined in Pure Appl. Chem., Vol. 83, No. 10, pp. 1831-1871, 2011. Semi-crystalline polymer refers to a polymer that has or can have regions of crystalline molecular structure and amorphous regions. The crystalline regions may be referred to as crystallites, lamella, or spherulites which can be dispersed or embedded within amorphous regions.

The "degree of crystallinity" may be expressed in terms of, $w_c$ (mass fraction), $\varphi_c$ (volume fraction) and refers to mass fraction or volume fraction of crystalline phase in a sample of polymer. The mass-fraction and the volume-fraction degrees of crystallinity are related by the equation, $w_c = \phi_c \rho / \rho_c$, where $\rho$ and $\rho_c$ are the mass concentrations (mass densities) of the entire sample and of the crystalline phase, respectively. The degree of crystallinity can be determined by several experimental techniques. Among the most commonly used are: (i) x-ray diffraction, (ii) calorimetry, (iii) mass density measurements, (iv) infrared spectroscopy (IR), (v) solid-state NMR spectroscopy, and (vi) vapor permeability.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

The "melting temperature" (Tm) is the temperature at which a material changes from solid to liquid state. In polymers, Tm is the peak temperature at which a semicrystalline phase melts into an amorphous state. Such a melting process usually takes place within a relative narrow range (<20° C.), thus it is acceptable to report Tm as a single value.

"Elastic deformation" refers to deformation of a body in which the applied stress is small enough so that the object retains, substantially retains, or moves towards its original dimensions once the stress is released.

The term "plastic deformation" refers to permanent deformation that occurs in a material under stress after elastic limits have been exceeded.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" and "stiffness" may be defined as the ratio of a component of stress or force per unit area applied to a material divided by the strain along an axis of applied force that result from the applied force. The modulus or the stiffness typically is the initial slope of a stress-strain curve at low strain in the linear region. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

A radial strength test measures the radial compressive pressure required to exceed the radial strength of the scaffold. Radial strength tests may be conducted on scaffolds using an MSI RX550 Radial Force Tester. Using this machine the scaffold is compressed circumferentially to a specified end diameter and compression dies within the tester record the radial force/pressure as a function of diameter. The rate of compression is 0.02 mm/sec. The scaffold is received crimped to a balloon of a balloon catheter. The scaffold is deployed on the balloon to the rated burst pressure in water at body temperature. The scaffold is compressed in air at body temperature. The radial yield strength is found from a computed modulus vs. diameter curve, which is calculated and reported as the radial stiffness. The radial strength is then reported as the maximum pressure (e.g., in millimeters of Mercury, abbreviated as "mm Hg") between the start of compression and where a 0.1 mm offset to the modulus intersects the pressure vs. diameter curve.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of a fabricating a scaffold comprising:
   forming a tube having an initial diameter made of a bioresorbable polymer by extrusion;
   after forming the tube, radially expanding the tube from the initial diameter to an expanded diameter, wherein the radial expansion step increases a crystallinity of the tube, and wherein the expanded tube has a thickness;
   elongating the expanded tube to a predetermined axial strain along its cylindrical axis by applying a tensile force to the expanded tube along its cylindrical axis, wherein the elongating decreases the thickness of the tube;
   thermally processing the elongated tube while the tube is fixed at the predetermined axial strain for a selected time at a temperature between a glass transition temperature (Tg) of the polymer and a melting temperature (Tm) of the polymer, wherein the thickness of the tube after the thermal processing is less than the thickness of the expanded tube,
   wherein the thermal processing increases the thickness of the tube to a desired thickness of 80 to 120 microns,
   wherein the predetermined axial strain is adjusted so that the decrease in thickness from the elongating and the increase in thickness from the thermal processing results in the desired thickness; and
   cutting a scaffold pattern in the thermally processed tube to form the scaffold.

2. The method of claim 1, wherein the elongating is performed at a temperature between Tg and Tm of the polymer.

3. The method of claim 1, wherein the selected time is 5 min to 20 min.

4. The method of claim 1, wherein a weight average molecular weight (Mw) of the polymer is 200 to 600 kDa.

5. The method of claim 1, wherein an Mw of the polymer is 600 to 1500 kDa.

6. The method of claim 1, wherein the thickness of the expanded tube is between 140 and 180 microns.

7. The method of claim 1, wherein the crystallinity of the tube prior to elongating is 20 to 50%.

8. The method of claim 1, wherein the elongating and thermal processing increase the crystallinity of the polymer by 1 to 10%.

9. The method of claim 1, wherein the elongating and thermal processing increase a strength and modulus of the polymer.

10. The method of claim 1, wherein the predetermined axial strain is 5 to 25%.

11. The method of claim 1, wherein the expanded diameter of the tube is fixed during the elongating and thermal processing.

12. The method of claim 1, wherein the expanded diameter of the tube decreases by no more than 1% during the elongating and thermal processing.

13. The method of claim 1, wherein the expanded diameter of the tube decreases by at least 1 and no more than 10% during the elongating and thermal processing.

14. The method of claim 1, further comprising disposing the expanded tube over a mandrel having a diameter less than the expanded diameter, wherein the expanded diameter of the tube decreases to the diameter of the mandrel during the elongating and thermal processing.

15. The method of claim 1, wherein the polymer is poly(L-lactide) (PLLA).

16. The method of claim 1, wherein the polymer is a blend of PLLA and poly(L-lactide-co-caprolactone).

* * * * *